(12) United States Patent
West, Jr.

(10) Patent No.: US 6,953,463 B2
(45) Date of Patent: Oct. 11, 2005

(54) INTERFERENCE SCREWS HAVING INCREASED PROXIMAL DIAMETER

(75) Inventor: Hugh S. West, Jr., Salt Lake City, UT (US)

(73) Assignee: HS West Investments, LLc, Salt Lake City, UT (US)

( * ) Notice: Subject to any disclaimer, the term of this patent is extended or adjusted under 35 U.S.C. 154(b) by 178 days.

(21) Appl. No.: 09/977,154

(22) Filed: Oct. 12, 2001

(65) Prior Publication Data

US 2003/0074002 A1   Apr. 17, 2003

(51) Int. Cl.$^7$ ........................ A61B 17/56; A61B 17/58; A61F 2/30
(52) U.S. Cl. ........................................ 606/73
(58) Field of Search ............................ 606/60, 62, 65, 606/72, 73, 232; 623/13.14; 411/421, 426, 411/395, 411, 412, 414

(56) References Cited

U.S. PATENT DOCUMENTS

| | | | | |
|---|---|---|---|---|
| 2,382,019 A | * | 8/1945 | Miller | 411/378 |
| 4,059,102 A | | 11/1977 | Devas | |
| 4,463,753 A | * | 8/1984 | Gustilo | 606/73 |
| 4,963,144 A | * | 10/1990 | Huene | 606/73 |
| 5,062,843 A | | 11/1991 | Mahony, III | |
| 5,139,499 A | | 8/1992 | Small et al. | |
| 5,151,104 A | | 9/1992 | Kenna | |
| 5,234,430 A | * | 8/1993 | Huebner | 606/60 |
| 5,259,398 A | | 11/1993 | Vrespa | |
| 5,282,802 A | | 2/1994 | Mahony, III | |
| 5,336,225 A | | 8/1994 | Zang | |
| 5,360,448 A | * | 11/1994 | Thramann | 606/60 |
| 5,364,400 A | | 11/1994 | Rego, Jr. et al. | |
| 5,505,731 A | | 4/1996 | Tornier | |
| 5,536,127 A | | 7/1996 | Pennig | |
| 5,573,548 A | * | 11/1996 | Nazre et al. | 606/232 |
| 5,607,428 A | | 3/1997 | Lin | |
| 5,653,710 A | | 8/1997 | Härle | |
| 5,693,055 A | | 12/1997 | Zahiri et al. | |
| 5,743,912 A | | 4/1998 | Labille et al. | |
| 5,925,048 A | * | 7/1999 | Ahmad et al. | 606/73 |
| 5,951,560 A | | 9/1999 | Simon et al. | |
| 5,964,766 A | | 10/1999 | Shaw | |

(Continued)

FOREIGN PATENT DOCUMENTS

EP   0669110   8/1995

(Continued)

OTHER PUBLICATIONS

"Tri-Cortical ACL Soft Tissue Graft Fixation", Arthrex. Published at least as early as Oct. 2001.

Primary Examiner—Kevin Shaver
Assistant Examiner—Anu Ramana
(74) Attorney, Agent, or Firm—Workman Nydegger (57) ABSTRACT

An interference screw for affixing soft tissue grafts during anterior cruciate ligament (ACL) reconstruction comprises a threaded body axially extending between a face and a tip along a central axis, with the face advantageously being obliquely aligned with the central axis. The threaded body includes a proximal threaded section and a distal threaded section, each of which may be straight or tapered. The proximal threaded section is approximately 1 mm larger in diameter than the distal threaded section. The increased diameter of the proximal threaded section enables the interference screw to compressively secure the soft tissue graft against the cortical bone, while the distal threaded section compresses the soft tissue graft against the cancellous bone with an appropriately reduced force that is appropriate for facilitating bonding of the soft tissue graft to the cancellous bone and that is sufficient for minimizing any "bungee effect."

32 Claims, 5 Drawing Sheets

U.S. PATENT DOCUMENTS

| | | | |
|---|---|---|---|
| 5,964,768 A | 10/1999 | Huebner | |
| 5,968,045 A | 10/1999 | Frazier | |
| 5,997,541 A * | 12/1999 | Schenk | 606/73 |
| 6,001,100 A | 12/1999 | Sherman et al. | |
| 6,001,101 A | 12/1999 | Augagneur et al. | |
| 6,015,937 A * | 1/2000 | Branemark | 623/16 |
| 6,019,759 A | 2/2000 | Rogozinski | |
| 6,030,162 A | 2/2000 | Huebner | |
| 6,036,491 A * | 3/2000 | Hansson | 433/174 |
| 6,045,554 A * | 4/2000 | Grooms et al. | 606/73 |
| 6,083,227 A * | 7/2000 | Saurat et al. | 606/73 |
| 6,206,925 B1 * | 3/2001 | Tornier | 623/19.12 |
| 6,214,031 B1 * | 4/2001 | Schmieding et al. | 606/232 |
| 6,306,140 B1 * | 10/2001 | Siddiqui | 606/73 |
| 6,319,254 B1 * | 11/2001 | Giet et al. | 606/73 |
| 6,368,322 B1 * | 4/2002 | Luks et al. | 606/73 |
| 6,387,129 B2 * | 5/2002 | Rieser et al. | 623/13.14 |
| 6,468,277 B1 * | 10/2002 | Justin et al. | 606/65 |
| 6,565,566 B1 * | 5/2003 | Wagner et al. | 606/61 |
| 6,589,245 B1 * | 7/2003 | Weiler et al. | 606/73 |
| 6,599,289 B1 * | 7/2003 | Bojarski et al. | 606/60 |
| 6,629,977 B1 * | 10/2003 | Wolf | 606/73 |
| 2002/0052605 A1 * | 5/2002 | Grooms et al. | 606/72 |
| 2002/0165546 A1 * | 11/2002 | Goble et al. | 606/72 |
| 2002/0193799 A1 * | 12/2002 | Chappius et al. | 606/80 |

FOREIGN PATENT DOCUMENTS

| | | |
|---|---|---|
| EP | 1 101 459 A2 | 5/2001 |
| EP | 0611557 | 8/2004 |
| FR | 2732211 | 10/1996 |
| FR | 2745999 | 9/1997 |

* cited by examiner

INTERFERENCE SCREWS HAVING INCREASED PROXIMAL DIAMETER

BACKGROUND OF THE INVENTION

1. The Field of the Invention

The present invention generally relates to the field of joint repair surgery, such as reconstruction of the anterior cruciate ligament (ACL). More particularly, the invention relates to the field of interference screws used generally for fixation of soft tissue grafts, such as tibial affixation of soft tissue ACL grafts.

2. The Relevant Technology

Injuries to joints, specifically the knee, are quite common, particularly when one engages in vigorous sporting activities. A common injury is a rupture or tear of the anterior cruciate ligament (ACL), which is the primary ligament responsible for holding the knee joint together and which keeps it from slipping out of joint or dislocating. An unrepaired ruptured or torn ACL can cripple, and would most certainly limit physical activity of, the person suffering a ruptured or torn ACL. Absent reconstruction of the ACL, such injuries would likely be the end of professional sports careers and would prevent ordinary people from enjoying an active life involving sports and like recreation.

Improvements in surgical procedures have made ACL reconstruction procedures more successful and, hence, more common. One method for performing an ACL reconstruction procedure involves taking a tissue graft from another part of the body, such as a soft tissue graft (e.g., from the hamstrings), and attaching it at both ends through bone tunnels drilled through the two bones that make up the knee joint: the femur and the tibia. When secured in place, the tissue graft mimics and, hence, takes the place of, the ACL itself. This tissue graft holds the femur and tibia together to make the joint more stable, while simultaneously allowing for normal joint movements (i.e., flexion and extension).

Graft tension in ACL reconstruction has been recognized as an important factor in the clinical outcome of the ACL reconstruction procedure. In other words, grafts that are too loose may be unstable while grafts that are too tight may restrict motion of the knee.

One particular problem associated with soft tissue grafts, commonly referred to as the "bungee effect," generally comprises excessive elasticity of the graft. The "bungee effect" occurs when the graft is affixed to the exterior surface of the bone, adjacent to the bone tunnel entrance, resulting in an effective graft length spanning not only the inside of the joint, but the length of the bone tunnel as well. The longer the graft, the more elastic the graft becomes. Accordingly, the "bungee effect" is accentuated with longer grafts. One method for minimizing the "bungee effect" is to utilize interference screws that shorten the effective length of the graft.

Interference screws are screwed into the bone tunnels through which the soft tissue graft passes, thereby causing the graft to be compressed against the surfaces of the bone tunnels with sufficient force for holding the graft in place. The interference screws shorten the effective length of the graft and minimize the "bungee effect" by affixing the soft tissue graft and preventing the graft from stretching inside of the bone tunnels.

Interference screws compress the graft against the exterior cortical bone regions, which are hard, as well as the interior cancellous bone regions, which are soft. To create sufficient pressures for holding the graft in place within the bone tunnels, particularly within the soft internal cancellous bone regions, interference screws are configured with diameters that are larger than the diameters of the bone tunnels. This enables the interference screw to compress the graft against the surface of the bone tunnel with sufficient force to hold the graft in place, where it ultimately bonds to the bone.

One problem with existing interference screws, however, is they often comprise bodies with substantially uniform diameters. This is a problem because it causes the interference screw to either exert too much pressure on the graft within the cancellous bone regions, thereby inhibiting healing and bonding of the graft to the bone, or alternatively, the interference screw exerts too little pressure on the graft within the cortical bone regions, thereby potentially resulting in insufficient holding strength for securing the graft in place.

Some existing interference screws are configured with a uniform taper spanning the entire length of the interference screws. These interference screws are also problematic. In particular, if the taper is very slight then the benefits of the taper are negligible and the pressures in the cancellous bone regions may remain too great. In contrast, a noticeable, or significant taper may result in insufficient compression of the graft for securing the graft in place, which is necessary for minimizing the "bungee effect" and for enabling the graft to bond with the bone.

Yet another problem with existing interference screws is that their trailing ends, or heads, are substantially flat and perpendicular with the body of the interference screw. This is generally a problem, as will be described below, because it is desirable for the interference screw to make complete circumferential contact with the cortical bone regions of the bone tunnel even though the bone tunnel is formed at an angle.

The strongest bone available for interference fixation of the graft is the cortical bone, which is located at and just beneath the surface of the bone. Accordingly, to maximize the screw fixation of the graft, the screw must optimally make complete circumferentially contact along the entire cortical bone region of the bone tunnel, including the exterior aperture of the bone tunnel. This is difficult, however, because the bone tunnels for tibial affixation of soft tissue grafts are formed at an angle, typically within the range of approximately 35° to approximately 40°. Due to the angle of the bone tunnel and the head configuration of existing screws, as described above, it is impossible for the screws to make complete circumferential contact along the entire cortical bone region of the bone tunnel when the screw is inserted entirely within the bone tunnel. Accordingly, if the trailing end of the screw is inserted completely within the bone tunnel, then fixation strength is compromised. Therefore, in order to obtain maximum cortical contact and fixation strength, existing interference screws can only be inserted within the bone tunnel to the point where the head of the interference screw starts to enter the bone tunnel, thereby resulting in a portion of the interference screw protruding out of the bone tunnel. This is a problem because protrusions can cause irritation and other problems for the patient, and therefore need to be removed with a cutting or grinding device, thereby increasing the risk, time, and cost associated with performing the ACL surgery.

In light of the foregoing, there is currently a need in the art of joint repair and soft tissue graft affixation to provide an improved interference screw that is configured to be inserted into obliquely aligned bone tunnels and for appropriately distributing within the bone tunnel the compressive forces that are used to hold the graft in place at the cancellous and cortical bone regions.

SUMMARY OF PRESENTLY PREFERRED EMBODIMENTS

Briefly summarized, presently preferred embodiments of the present invention are directed to improved interference screws for affixing soft tissue grafts within tibia bone tunnels for ACL reconstructive surgery.

According to one preferred embodiment, the interference screws of the invention comprise a threaded body axially extending between a face and a tip along a central axis. The threaded body includes proximal and distal sections, with the proximal section generally having a larger diameter than the distal section. The proximal and distal sections may comprise constant diameters, or varying diameters and tapers. The proximal section is located proximate the face and the distal section is located proximate the tip. According to one preferred embodiment, the proximal and distal sections are cylindrical such that each comprises constant outer diameters, with the outer diameter of the distal cylindrical section being less than the outer diameter of the proximal cylindrical section.

The proximal cylindrical section is configured in size and shape for applying compressive forces at the exterior cortical bone regions of the bone tunnel while the distal cylindrical section is configured in size and shape for applying compressive forces at the interior cancellous bone regions of the bone tunnel. Because the diameter of the proximal cylindrical section is greater than the diameter of the distal cylindrical section, the compressive forces applied within the cortical bone regions are greater than the compressive forces applied within the cancellous bone regions. The increased compression in the cortical bone region enables the interference screw to more securely hold the graft in place, while the reduced compression in the cancellous bone regions promotes the bonding of the soft tissue graft with bone. It will be appreciated, however, that although the compressive forces applied by the distal cylindrical section are reduced, they are still sufficient to help hold the soft tissue graft in place for minimizing the "bungee effect." Accordingly, it will be appreciated that this embodiment is useful for enabling the interference screw to secure the soft tissue graft in place within the bone tunnel while, at the same time, facilitating bonding of the soft tissue graft to the tibia.

According to one preferred embodiment, the proximal threaded section includes an angled face extending from a circumferential edge on one side to the proximal end of the screw at the opposite side. The angle of the face advantageously corresponds to the angle of the bone tunnel relative to the surrounding bone surface. This enables the face of the interference screw to lay substantially flush with, or parallel to, the surrounding bone surface when the interference screw is completely inserted within the tibial bone tunnel at an appropriate rotational angle. Accordingly, in those cases where the bone tunnel is not perpendicular to the surrounding bone surface, the face of the interference screw may advantageously have any appropriate angle less than 90° relative to the central axis. In most cases, the angle of the face may range from about 10° to about 80° relative to the central axis, more preferably in a range of about 20° to about 60°. Based on the most common angles of bone tunnels used in ACL repair operations, the face of the interference screw may be more preferably angled relative to the central axis in a range of about 30° to about 40° and, most preferably, at an angle of about 35°.

Inasmuch as the interference screw is inserted within the body, the interference screw preferably comprises a material composition that is biodegradable, biocompatible and/or biointegratable. According to one preferred embodiment, the interference screw is composed of poly-l-lactic acid (PLLA). It will be appreciated, however, that the interference screw may also be composed of other suitable materials, such as bio-compatible plastics and bio-compatible metals including, but not limited to titanium, and stainless steel.

To facilitate insertion of the interference screw within the bone tunnel, the interference screw further includes a recess comprising a drive socket that axially extends at least partially into the proximal section of the interference screw. The drive socket is preferably configured to receive the corresponding shaft of a driver, such as an interference screw driver, that can be used to screw the interference screw into the bone tunnel.

To further facilitate insertion of the interference screw into the bone tunnel, the tip of the interference screw may be tapered and/or pointed. According to an alternative embodiment, the proximal and distal sections of the interference screw are also tapered. The tapers may be the same, being defined by the same angle, or alternatively, the tapers may vary, being defined by different angles. According to one embodiment, for example, the taper of the proximal section may be less pronounced than the taper of the distal section.

According to yet another embodiment, only one of the proximal and distal sections comprises a taper, with the other of the proximal or distal sections comprising a constant diameter with no taper.

Each of the proximal and distal sections as well as the tip are threaded, thereby enabling the interference screw to engage the soft tissue graft within the bone tunnel, and thereby enabling the interference screw to securely hold the soft tissue graft in place within the bone tunnel. It will be appreciated that the threads of the proximal and distal sections may comprise the same pitch or a different pitch. The threads of the proximal and distal sections may also be continuously joined into a single thread, or alternatively, the threads of the proximal section and the distal section may be discontinuous and separated by a space.

During use, the interference screw of the invention is used to securely affix a soft tissue graft within a bone tunnel formed within the tibia near the knee joint. A special device may be used to align the interference screw and to ensure that the interference screw is properly threaded and inserted into the bone tunnel.

The interference screw of the invention is beneficial for at least enabling soft tissue grafts to be securely affixed within the cortical bone regions of a bone tunnel while, at the same time, facilitating or promoting the bonding of the soft tissue grafts against the inner surface of the bone tunnel. This is possible because of the different diameters and/or tapers existing between the proximal and distal sections of the interference screw. The obliquely aligned face of the interference screw also minimizes the potential risk, time and cost, associated with trimming off any protrusions extending out of the bone tunnel once the interference screw has been inserted into place.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof, which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

The present invention is directed to improved interference screws for affixing a soft tissue graft within a bone to tunnel, such as within bone tunnel in the tibia for ACL reconstructive surgery. Such interference screws comprise a threaded body axially extending between a proximal end and a distal end along a central axis. The threaded body includes proximal and distal threaded sections having differing diameters, with the proximal section generally having a larger average diameter than the distal section. The proximal and distal threaded sections may comprise constant diameters, such that the outer diameter of each section is substantially cylindrical, or they may have varying diameters such that at least part of each section includes a taper (i.e., is angled rather than parallel to the central axis). One threaded section may be cylindrical and the other section at least partially tapered.

The proximal threaded section may include an angled face corresponding to the angle of the bone tunnel into which the interference screw is to be inserted. In this way, the angled face will be able to lie approximately flush with the bone surface surrounding the bone tunnel, or at least lie parallel thereto, in order to reduce or eliminate any significant protrusion by the interference screw above the bone surface when completely inserted within the bone tunnel during fixation of a soft tissue graft.

For purposes of this disclosure and the appended claims, the term "outer diameter" shall in all cases, unless otherwise specified, be understood as being twice the radius from the central axis, at any given point along the axis, to the outer edge of the nearest thread. Thus, in those embodiments that include an angled face such that a portion of the threaded proximal section has been removed or omitted, the "diameter" shall be deemed to be twice the radius, unless otherwise specified. The term "average diameter" shall be the mean major (i.e., outer) diameter of either the proximal or distal threaded section (but excluding the diameter of the tip of the distal threaded section if tapered), whether or not the diameter within a particular section is constant. In a preferred embodiment the thread depth will be constant such that the minor diameter (i.e., the root diameter) of the screw generally follows the major diameter.

The interference screws preferably have a single continuous thread of continuous uniform pitch wrapping around the outer perimeter of the threaded body. The distal tip, particular if tapered, may or may not be entirely threaded. For purposes of this disclosure and the appended claims, the term "continuous" thread, unless otherwise specified, shall be understood as pertaining even to the technically discontinuous threads of a proximal threaded section that has an angled face (i.e., in which a portion of the threads have been removed or omitted from the face side) so long as the remaining threads line up with, or are positioned in the same place as, the continuous thread that would otherwise exist, but for the angled face. The continuous thread preferably includes a constant thread depth (i.e., the radial distance between the outer edge and root of the thread) throughout at least a portion of the screw, although the thread depth may vary at the distal end if tapered, and it may vary, if desired, at the transition between the distal and proximal threaded sections.

It is also within the invention to provide interference screws that include no threads along a particular length of screw about the circumference (e.g., discontinuous threads, such as a non-threaded transition section between the proximal and distal threaded sections, a non-threaded distal tip, or a non-threaded section at the proximal end. It is also within the scope of the invention to provide interference screws of varying thread pitch, although such embodiments would be less preferred, as would embodiments that included a non-threaded transition section.

The interference screws disclosed herein are examples of interference screws that have a "discontinuous taper". The term "discontinuous taper" may include other variations and configurations that do not define screws with continuous taper, such as those disclosed in U.S. Pat. No. 5,964,768 to Huebner and EP 1101 459 to Wolf.

Reference will now be made to figures wherein like structures will be provided with like reference designations.

Figure 1:
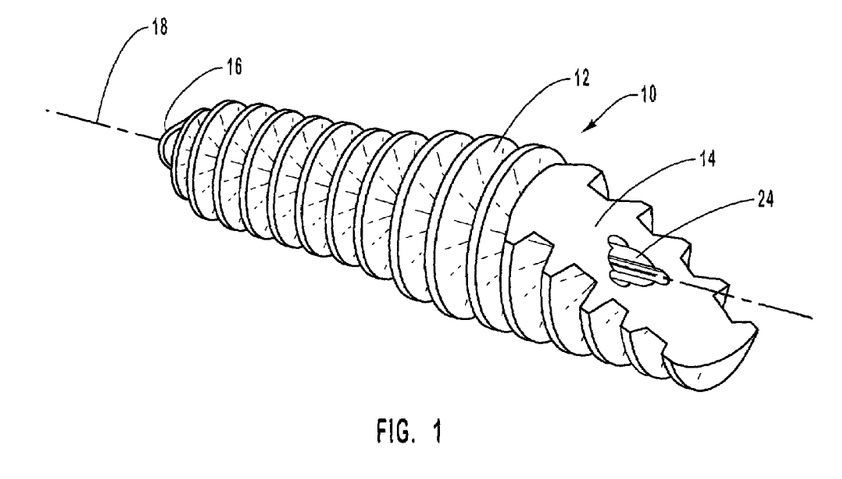
FIG. 1 is a perspective view of one preferred embodiment of the interference screw of the present invention having proximal and distal threaded sections that are generally cylindrical, a tapered tip, a face obliquely aligned with a central axis of the interference screw, and a drive socket extending into the body of the interference screw.

Reference is first made to FIG. 1, which illustrates one presently preferred embodiment of the interference screw of the invention. As shown, the interference screw 10 comprises a threaded body 12 axially extending between a face 14 and a tip 16 along a central axis 18. The tip is preferably tapered to facilitate entry of the interference screw 10 into a bone tunnel.

Inasmuch as the interference screw is inserted within the body, the interference screw preferably comprises a material composition that is biodegradable, biocompatible and/or biointegratable. According to one preferred embodiment, the interference screw is composed of poly-l-lactic acid (PLLA). It will be appreciated, however, that the interference screw may also be composed of other suitable materials, such as bio-compatible plastics and bio-compatible metals including, but not limited to titanium and stainless steel.

According to one preferred embodiment, the face 14 of the interference screw 10 is preferably aligned relative to the central axis 18 at an angle that corresponds with the angle at which the bone tunnel is formed in the tibia. It will be appreciated that this enables the face 14 of the interference screw 10 to lay substantially flush with the exterior surfaces of the tibia through which the bone tunnel is formed when the screw 10 is completely inserted into a bone tunnel and oriented at an appropriate rotational angle.

For purposes of this disclosure and the appended claims, the term "completely inserted", when used in conjunction with the insertion of an interference screw into a bone tunnel, shall be understood to mean an interference screw that has been threadably inserted into the bone tunnel to a depth so that a face of the interference screw may lie approximately flush with the bone surface surrounding the opening into the bone tunnel, either because the face of the interference screw is angled so as to lie flush with the bone surface when the interference screw is at an appropriate rotational angle or by removing a portion of the interference screw after complete insertion.

In most cases where the bone tunnel is not perpendicular to the surrounding bone surface, the face of the interference screw may advantageously have any appropriate angle less 90° relative to the central axis. In most cases, the angle of the face may range from about 10° to about 80° relative to the central axis, more preferably in a range of about 20° to about 60°. Based on the most common angles of bone tunnels used in ACL repair operations, the face of the interference screw may be more preferably angled relative to the central axis in a range of about 30° to about 40° and, most preferably, in an angle of about 35°.

Figure 2:
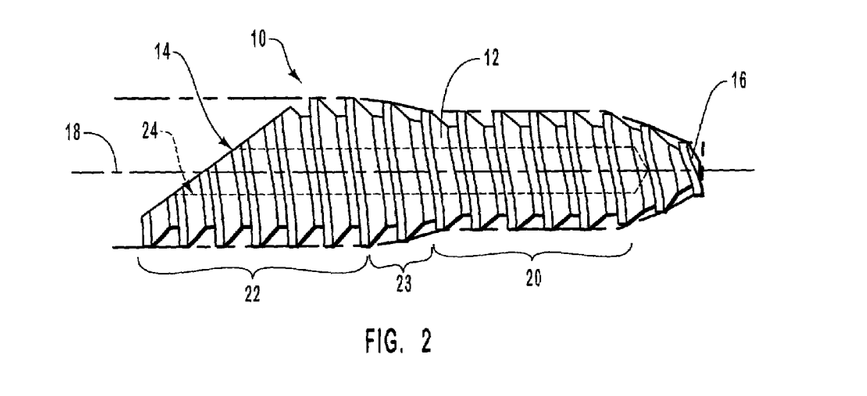
FIG. 2 is a side view of the interference screw of FIG. 1 showing the profile of the proximal and the distal threaded sections, each of which have different and constant diameters.

As shown in FIG. 2, the threaded body 12 of the interference screw 10 comprises a distal threaded cylindrical section 20 and a proximal threaded cylindrical section 22. The threads of the distal and proximal cylindrical sections 20,22 may comprise the same pitch or a different pitch. The threads of the distal and proximal cylindrical sections 20, 22 may also be continuously joined into a single thread or, alternatively, the threads of the distal cylindrical section 20 and the proximal cylindrical section 22 may be discontinuous and separated by a space.

As shown, the diameter of the distal threaded cylindrical section 20, which is proximate the tapered tip 16, is smaller than the diameter of the proximal threaded cylindrical section 22, which is located proximate the face 14. The term "diameter" as used herein will generally refer to the outer diameter defined by the outer edge of the threads, although it will also refer to twice the radius in the case where a portion of the screw has been removed or omitted, such as in the case of an obliquely angled face. According to one preferred embodiment, the diameter of the distal threaded cylindrical section 20 is preferably within the range of approximately 9 mm to approximately 11 mm, and the diameter of the proximal threaded cylindrical section 22 is preferably within the range of approximately 10 mm to approximately 12 mm. According to one preferred embodiment, the diameter of the distal cylindrical section 20 is approximately 1 mm less than the diameter of the proximal cylindrical section 22. As shown, tapered transition section 23, which tapers from the proximal cylindrical section 22 down to the distal cylindrical section 20, may also be provided to join the distal cylindrical section 20 with the proximal cylindrical section 22 with a smooth transition.

The variation in diameter between the distal threaded section 20 and the proximal threaded section 22 enables the interference screw 10 of the invention to securely compress soft tissue grafts against the cortical bone regions of a bone tunnel while, at the same time, applying less pressure against the soft tissue graft within the cancellous bone regions of the bone tunnel. This is beneficial for enabling the soft tissue graft to quickly heal and bond with the bone in the cancellous bone regions.

According to one preferred embodiment, the length of the interference screw 10 is within the range of approximately 35 mm to approximately 40 mm. It will be appreciated, however, that the length of the interference screw 10 may comprise any desired length for accommodating various needs and preferences. It will also be appreciated that the lengths and diameters of the distal and proximal sections 20, 22 may vary. For example, according to one preferred embodiment, the length of the proximal end 22 is specifically configured to accommodate the thickness of the cortical bone region of the tibia, which is approximately 5 mm thick, but which may vary between different patients.

Figure 3:
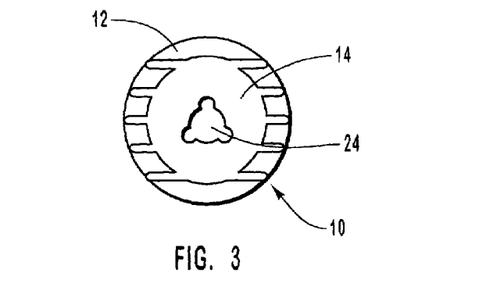
FIG. 3 illustrates an end view of the interference screw of FIG. 1 showing the face and a drive socket extending into the interference screw that is configured for receiving the shaft of a driver comprising three radially extending protrusions.

An end view of the interference screw 10 showing the face 14 is illustrated in FIG. 3. As shown in FIG. 3, as well as in FIGS. 1 and 2, a drive socket 24 axially extends into the interference screw 10. The drive socket 24 may extend only partially into the body 12 of the interference screw 10 or, alternatively, the drive socket 24 may extend all the way through the proximal section 22 and into the distal section 20, as shown in FIG. 2. The drive socket 24 may also extend entirely through both the proximal and distal sections 20, 22. Additionally, an axial bore (not shown) may be provided for a guide wire, as will be understood by those skilled in the art.

The drive socket 24 is specifically configured for receiving the shaft of a driver that can rotatably screw the interference screw 10 into a bone tunnel. Inasmuch as the shaft of a driver may vary in shape, the shape of the drive socket 24 may also vary. According to one preferred embodiment, as shown in FIG. 3, the drive socket 24 comprises a shape that is configured for receiving the shaft of a typical interference screw driver having three radially extending protrusions.

Figure 4:
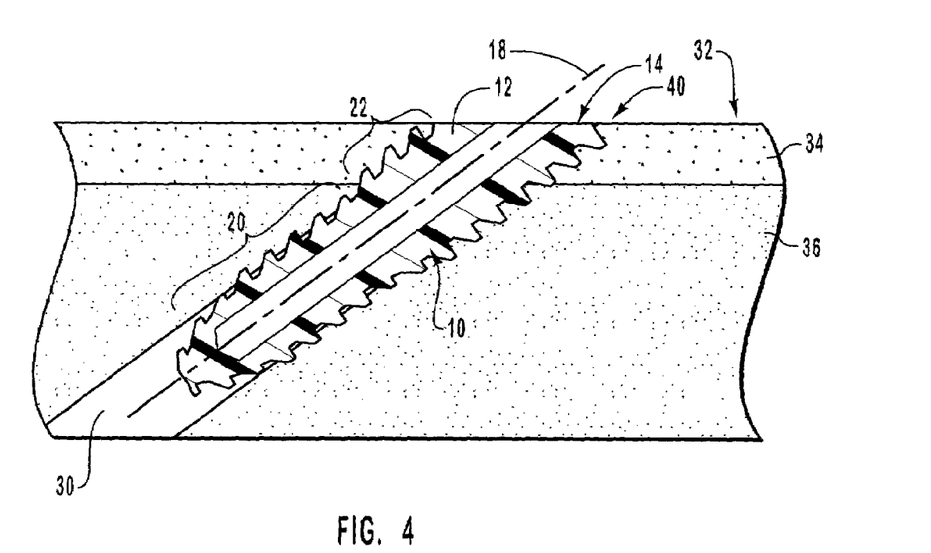
FIG. 4 illustrates a cross-sectional view of the interference screw of FIG. 1 inserted within a tunnel in a bone having a cortical bone region and a cancellous bone region.

Turning now to FIG. 4, a cross-sectional side view of the interference screw 10 is illustrated. As shown, the interference screw 10 is inserted within a bone tunnel 30 that is formed at an angle within the cortical and cancellous bone regions of a bone 32. The cortical bone region 34 comprises the exterior portions of the bone 32 and is harder than the cancellous bone region 36, which comprises the interior portions of the bone 32.

As shown in FIG. 4, the distal section 20 of the interference screw 10 is inserted within the cancellous bone region 36, while substantially all of the proximal section 22 of the interference screw 10 is inserted within the cortical bone region 34 of the bone 32. It will be appreciated, however, that according to some embodiments the proximal section 22 may be configured so that it extends at least partially into the cancellous bone regions 36.

During use, a soft tissue graft is inserted within the bone tunnel 30, and the interference screw 10 compresses the soft tissue graft between the threaded body 12 of the interference screw 10 and the bone 32. The interference screws of the invention are specifically configured for applying compressive forces to the soft tissue graft distinctly within the two regions of the bone tunnel. In particular, the distal section 20 compresses the soft tissue graft against the cancellous bone regions 36 of the bone tunnel 30, and the proximal section 22 compresses the soft tissue graft against the cortical bone regions 34 of the bone tunnel 30. This enables the interference screw 10 of the invention to securely affix the soft tissue graft at the cortical bone region 34 while at the same time applying less pressure to the soft tissue graft within the cancellous bone regions 36.

The pressures exerted by the distal section 20 on the soft tissue graft are sufficient to help hold the graft in place, thereby shortening the effective length of the graft and minimizing, or lessening the "bungee effect." However, because the diameter of the distal section 20 is reduced, the compressive forces exerted on the soft tissue graft within the cancellous bone regions 36 are reduced relative to those forces exerted by the proximal section 22, thereby promoting the healing and bonding of the soft tissue graft to the bone.

As shown in FIG. 4, the face 14 of the interference screw 10 lays substantially flush with an exterior surface 40 of the bone 32. This is possible because the face 14 is obliquely aligned with the central axis 18 of the interference screw 10 at approximately the same angle at which the bone tunnel 30 is formed into the bone 32. It will be appreciated by those skilled in the art that this minimizes the risks, time and costs associated with trimming or otherwise removing protrusions extending out of the bone tunnel 30 once the interference screw 10 has been inserted. To ensure that the interference screw 10 is centrally aligned within the bone tunnel 30, a special device (not shown) may be used to align the interference screw 10 during insertion.

In FIGS. 1–2 and 4, the distal and proximal sections 20 and 22 are shown to have constant diameters. It will be appreciated, however, that each of the distal and proximal sections 20 and 22 may comprise varying diameters, thereby defining a taper.

Figure 5:
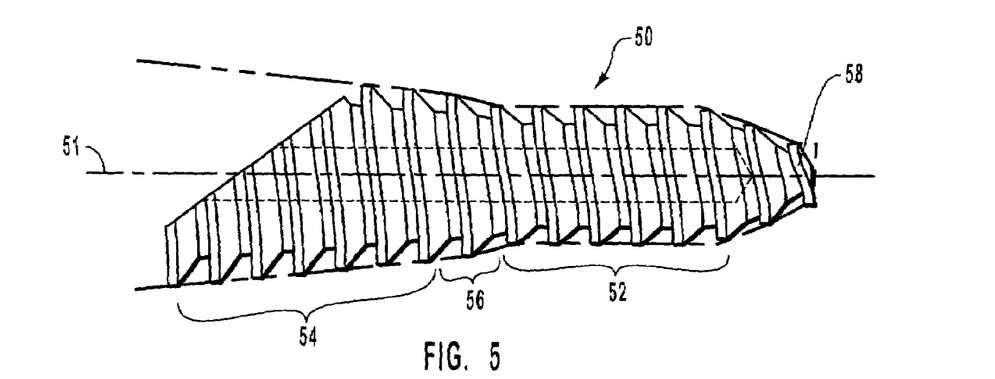
FIG. 5 illustrates an alternative embodiment of an interference screw of the invention that includes a distal, generally cylindrical, section having a constant diameter and a proximal section having a tapered, or changing, diameter.

For example, as shown in FIG. 5, the distal, generally cylindrical section 52 of interference screw 50 maintains a constant diameter, having no taper, while the proximal section 54 is tapered, having varying diameters. This embodiment may be useful for substantially increasing the compressive forces within a portion of the cortical bone region without substantially increasing the compressive forces within the cancellous bone regions. Although the proximal section 54 is shown to have a constant taper, it will be appreciated that the angle of the taper may alternatively vary to accommodate different needs and preferences. For example, as a matter of example and not limitation, the taper may be curved.

Figure 6:
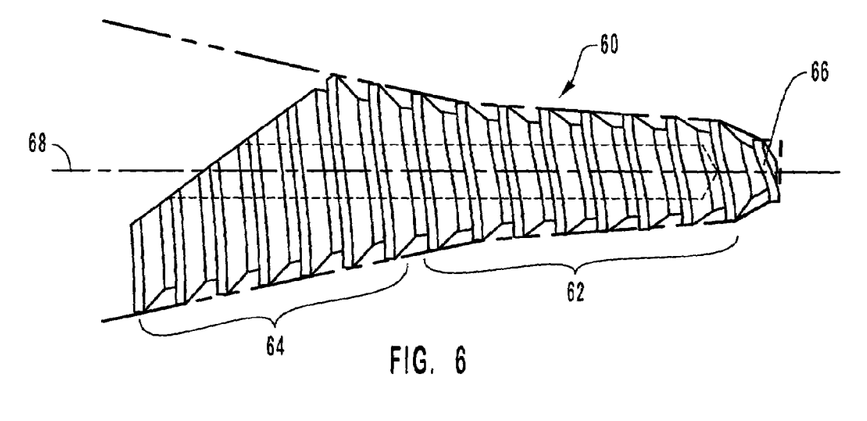
FIG. 6 illustrates another alternative embodiment of an interference screw of the invention that includes a proximal threaded section with a taper and a distal threaded section with a taper that is less pronounced than the taper of the proximal threaded cylindrical section.

According to another embodiment, as shown in FIG. 6, both the distal and proximal threaded sections 62 and 64 of interference screw 60 comprise a taper. As shown, the taper of the distal threaded section 62 is less pronounced than the taper of the proximal section 64. The embodiment shown in FIG. 6 may be desirable for gradually minimizing the pressures experienced within the bone tunnel near the tip of the interference screw 60, thereby enabling the soft tissue graft to more quickly heal and bond with the bone in the cancellous bone regions. Although the tapers of the distal and proximal cylindrical sections 62, 64 are shown to be different, such that they are defined by different angles of orientation relative to the central axis 68, it will be appreciated that the tapers of the distal and proximal cylindrical sections 62, 64 may also be the same (subject, of course, to the use of an appropriate transition section, if necessary).

Figure 7:
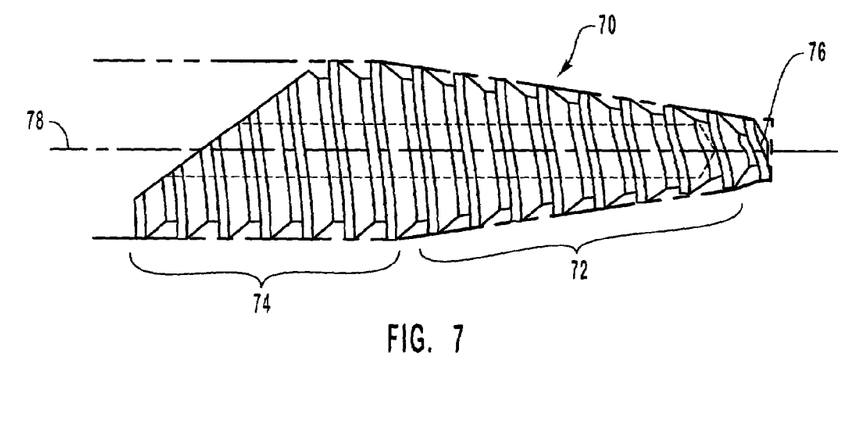
FIG. 7 illustrates an alternative embodiment of an interference screw of the invention in which the distal threaded section is tapered and the generally proximal, cylindrical section has a constant diameter.

According to yet another embodiment, shown in FIG. 7, the distal section 72 of interference screw 70 may comprise a taper, while the proximal, generally cylindrical section 74 comprises a constant diameter, having no taper. This embodiment may be desirable for creating substantially uniform compressive forces within the cortical bone regions of a bone tunnel with the proximal threaded cylindrical section 74, while at the same time minimizing the compressive forces applied to the soft tissue graft by the distal cylindrical section 72, particularly near the tip 76. For reasons described above, this is also useful for facilitating the healing and bonding of the soft tissue graft with the bone in the cancellous bone regions.

Figure 8:
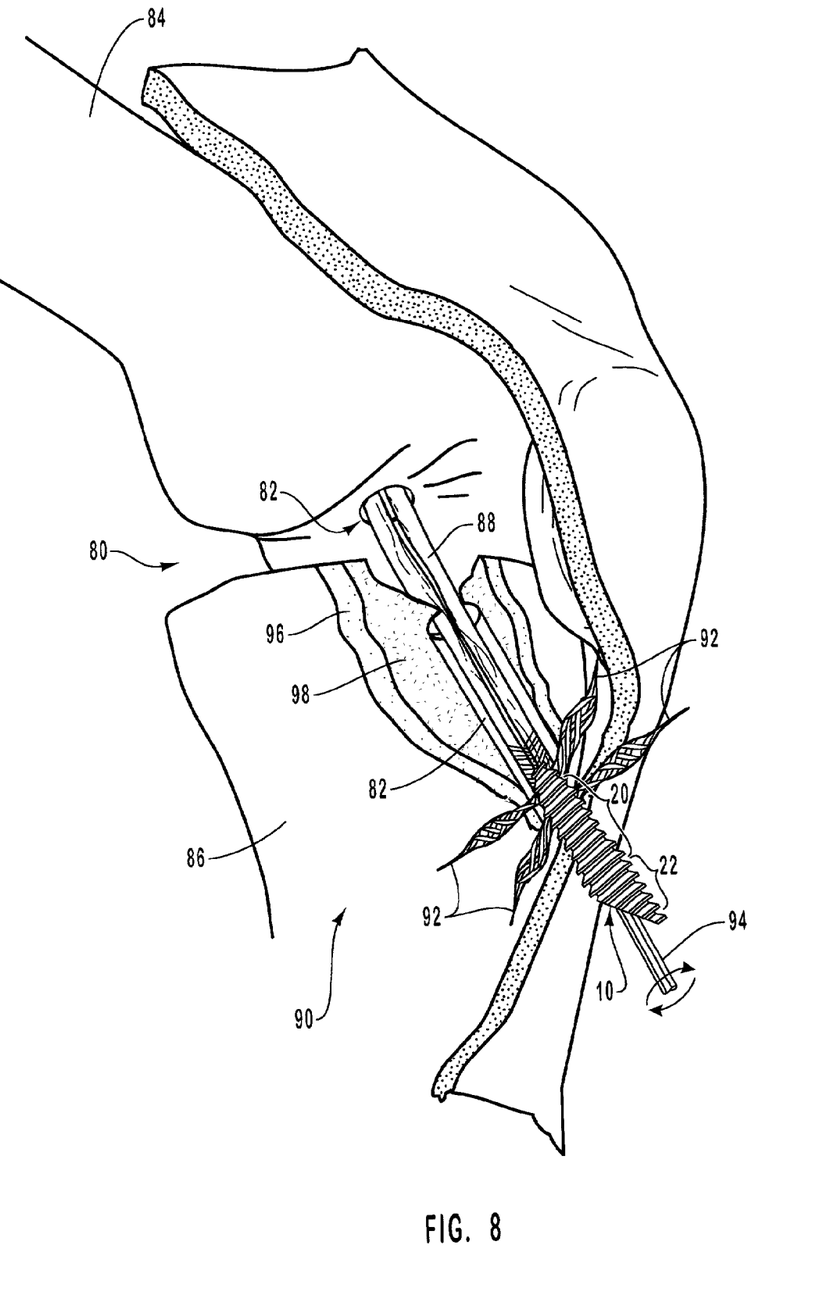
FIG. 8 illustrates a perspective view of a knee joint that includes the femur and the tibia, with a bone tunnel fashioned through the tibia and into the femur and a soft tissue graft inserted through the bone tunnel, and with an interference screw of the invention being inserted into the bone tunnel of the tibia.

Turning now to FIG. 8, a partial cross-sectional view of a knee joint 80 is shown. A bone tunnel 82 is formed at an angle into or through the femur 84 and through the tibia 86 of the knee joint 80. The bone tunnel formed through the tibia is preferably formed at an angle within the range of approximately 35° to approximately 40° relative to the bone surface.

During ACL reconstructive surgery, according to one embodiment, a soft tissue graft 88 is inserted through the bone tunnel 82 of the femur 84 and the tibia 86. According to the presently preferred embodiment, the soft tissue graft 88 comprises a hamstring graft. Hamstring grafts typically comprise multiple strands (e.g. four strands) and are well known in the art for ACL repair operations. Although a multi-strand hamstring graft may be used in the present example as one suitable soft tissue graft, it will be appreciated that the interference screws of the invention may be used to affix other appropriate soft tissue grafts comprising any number of strands. In appropriate circumstances an interference screw according to the invention may be used to affix bone-tendon-bone or other grafts.

The soft tissue graft 88 is initially passed through the tibial portion of the bone tunnel and secured within the bone tunnel 82 of the femur 84 with an interference screw or another device. Next, the soft tissue graft is pulled within the bone tunnel 82 within the tibia 86 and then properly tensioned to ensure that the graft will not be secured too loosely or too tightly. Special tensioning devices may be used to properly tension the strands of the soft tissue graft. U.S. patent application Ser. No. 09/711,488, entitled APPARATUS AND METHODS FOR INDEPENDENTLY CONDITIONING AND PRE-TENSIONING A PLURALITY OF LIGAMENT GRAFTS DURING JOINT REPAIR, filed on Nov. 13, 2000, discloses suitable tensioning devices and is incorporated herein by reference.

Once the soft tissue graft 88 has been properly tensioned, the soft tissue graft 88 can be secured to the tibia 86. The soft tissue graft 88 may, for example, be secured to the exterior surface 90 of the tibia 86. However, this may leave a portion of the soft tissue graft 88 unsecured within the bone tunnel 82, resulting in a "bungee effect." To minimize this "bungee effect," an interference screw of the present invention may be used to secure the soft tissue graft 88 within the bone tunnel 82 of the tibia 86, thereby reducing the effective length and elasticity of the soft tissue graft 88.

As illustrated in FIG. 8, the ends 92 of the soft tissue graft 88 have been tied, such as with a whip stitch, and are pulled apart so that an interference screw, such as interference screw 10, may be inserted within the bone tunnel 82 between the separate strands of the soft tissue graft 88. Alternatively, the graft may be positioned eccentrically within the bone tunnel 82. Once the interference screw has been properly positioned, a driver can be used to screw the interference screw into the bone tunnel 82 within the tibia 86. According to one preferred embodiment, a suitable driver includes a shaft, such as shaft 94, which can be inserted into the drive socket of the interference screw and can be used to screw the interference screw into the bone tunnel 82, as described above in reference to FIGS. 1–4.

Figure 9:
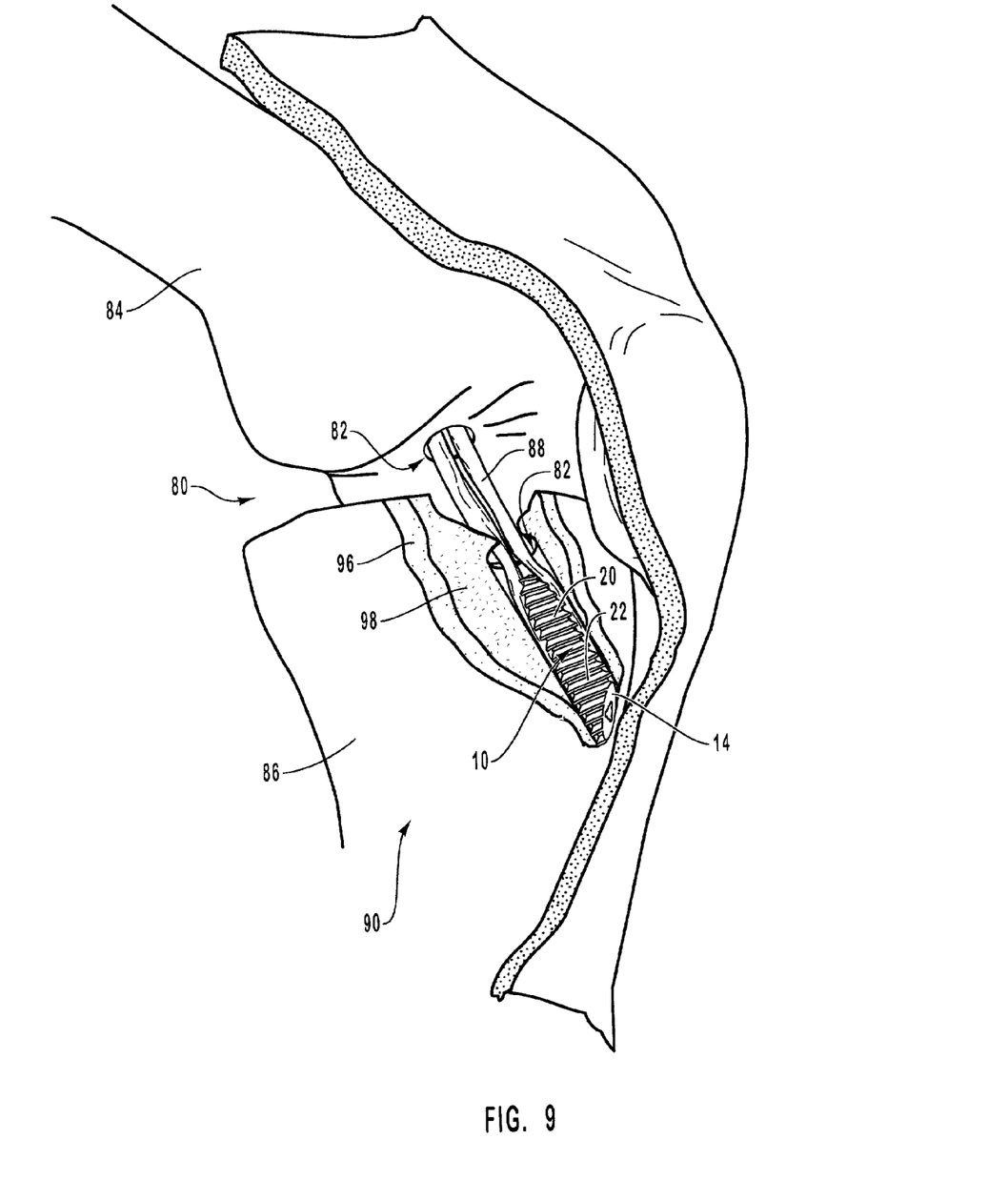
FIG. 9 illustrates the knee joint of FIG. 8 with the interference screw completely inserted within the bone tunnel such that the face of the interference screw is substantially flush with the exterior surface of the tibia and with the soft tissue graft compressed between the interference screw and the bone in the cortical and cancellous bone regions.

Turning now to FIG. 9, it is shown how an interference screw according to the invention can securely hold the soft tissue graft 88 in place within the bone tunnel 82 of the tibia 86. As shown, the interference screw 10 compresses the soft tissue graft 88 against the surfaces of the bone tunnel 82, thereby minimizing the effective length of the soft tissue graft 88 that may be stretched between the femur 84 and the tibia 86, and thereby minimizing, or lessening, the "bungee effect".

It will be appreciated that because the interference screws according to the invention comprise a distal section and a proximal section, each of which comprise different diameters and/or tapers, the interference screws are able to compress the soft tissue graft 88 against the cortical bone regions 96, securely holding the soft tissue graft in place, while at the same time compressing the soft tissue graft 88 against the cancellous bone regions 98, thereby facilitating the bonding and healing of the soft tissue graft 88 within the bone tunnel 82.

FIG. 9 also illustrates how once an interference screw 10 is inserted within the bone tunnel 82 at a desired placement, the face 14 of the interference screw 10 rests substantially flush with the exterior surface 90 of the tibia 86, thereby eliminating any need to trim off or remove protrusions that may otherwise have protruded out of the bone tunnel 82 and which could potentially create irritation and/or other problems for the patient.

In summary, the interference screws of the invention, as described herein, generally enable a soft tissue graft to be securely affixed within a bone tunnel extending through the tibia. The interference screws of the invention minimize or lessen the "bungee effect", while at the same time promote the healing and bonding of the soft tissue graft to the bone tunnel. In particular, the interference screws of the present invention comprise (1) a proximal section having an increased diameter for securely compressing the soft tissue graft against the cortical bone region with sufficient compressive forces for securing the soft tissue graft in place and (2) a distal section having a reduced diameter for compressing the soft tissue graft against the cancellous bone regions of the bone tunnel with compressive forces that are sufficient for minimizing the "bungee effect," but that are reduced compared to those exerted in the cortical bone region so as to promote healing of the graft to the bone. The interference screws of the invention also comprise a face that may be obliquely aligned with a central axis extending through the interference screws, thereby minimizing the need for reducing or removing any protrusions extending beyond the bone tunnel once the interference screws have been inserted into the bone tunnel.

It will be appreciated that the interference screws of the invention may be used in conjunction with special devices used for aligning the interference screw and for inserting the interference screws within bone tunnels with desired alignment and to desired depths.

The present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. An interference screw for cortical and cancellous bone fixation of a soft tissue graft within a bone tunnel, comprising:
   a threaded body extending between a proximal end and a distal end along a central axis and being sized and configured for threadable insertion into a bone tunnel, the threaded body further comprising:
   a proximal threaded section for cortical bone fixation comprising a proximal thread and having an average diameter; and
   a distal threaded section for cancellous bone fixation, disposed between the proximal threaded section and the distal end, comprising a distal tread and having a constant diameter that is less than the average diameter of the proximal threaded section,
   the distal threaded section having a length that is greater than the length of the proximal threaded section in order for the interference screw to apply force along a greater distance in the cancellous bone region compared to the cortical bone region,
   the proximal end having an angle relative to the central axis in a range of about 10° to about 80°,
   the proximal and distal threads having the same pitch.

2. An interference screw as defined in claim 1, further including a recess, centered on the central axis and extending from the proximal end at least partially through the interference screw, that is sized and configured to receive at least a portion of a drive shaft of a driver used to threadably insert the interference screw into a bone tunnel.

3. An interference screw as defined in claim 1, further including a tapered section disposed between the distal threaded section and the distal end that facilitates insertion of the distal end of the interference screw into a bone tunnel.

4. An interference screw as defined in claim 1, wherein the proximal threaded section is separated from the distal threaded section by a transition section.

5. An interference screw as defined in claim 4, wherein the transition section is threaded and tapered.

6. An interference screw as defined in claim 1, wherein the threaded body includes a single continuous thread of continuous pitch and helix angle extending between the proximal and distal ends, the interference screw optionally including a non-threaded portion adjacent at least one of the proximal or distal ends.

7. An interference screw as defined in claim 1, wherein the angle of the proximal end corresponds to an angle of a bone tunnel into which the interference screw is threadably inserted so that, upon threadably inserting the interference screw into a bone tunnel, the proximal end is substantially parallel to a bone surface surrounding the bone tunnel when the interference screw is oriented at an appropriate rotational angle.

8. An interference screw as defined in claim 1, wherein the proximal end has an angle relative to the central axis in a range of about 20° to about 60°.

9. An interference screw as defined in claim 1, wherein the proximal end has an angle relative to the central axis in a range of about 30° to about 40°.

10. An interference screw as defined in claim 1, wherein the proximal threaded section has a constant diameter.

11. An interference screw as defined in claim 1, wherein the proximal threaded section is at least partially tapered.

12. An interference screw as defined in claim 1, wherein the proximal threaded section of the interference screw is sized so as to lie substantially adjacent to cortical bone, and the distal threaded section is sized so as to lie substantially adjacent to cancellous bone, when the interference screw is completely inserted into a bone tunnel during use.

13. An interference screw as defined in claim 1, wherein the interference screw comprises at least one of poly-l-lactic acid, titanium, or stainless steel.

14. An interference screw as defined in claim 1, wherein the average diameter of the proximal treaded section is in a range of about 10 mm to about 12 mm and the average diameter of the distal threaded section is in a range of about 9 mm to about 11 mm.

15. An interference screw as defined in claim 1, wherein the avenge diameter of the proximal threaded section is about 1 mm greater than the average diameter of the distal threaded section.

16. An interference screw as defined in claim 1, wherein the interference screw has a length in a range of about 35-mm to about 40-mm.

17. An interference screw as defined in claim 16, wherein the proximal threaded section has a length of about 5 mm.

18. An interference screw for cortical and cancellous bone fixation of a soft tissue graft within a bone tunnel, comprising:
a threaded body extending between a proximal end and a distal end along a central axis and being sized and configured for threadable insertion into a bone tunnel, the threaded body further comprising:
a proximal threaded section sized and configured so as to lie primarily adjacent to cortical bone when the interference screw is completely inserted into a bone tunnel, the proximal threaded section having an average diameter;
a distal threaded section sized and configured so as to lie primarily adjacent to cancellous bone when the interference screw is completely inserted into a bone tunnel, the distal threaded section having a constant diameter that is less than the avenge diameter of the proximal threaded section,
the distal threaded section having a length that is greater than the length of the proximal threaded section in order for the interference screw to apply force along a greater distance in the cancellous bone region compared to the cortical bone region,
the proximal and distal threaded sections being configured in order for the interference screw to apply less pressure against a soft tissue graft within the cancellous bone region compared to the cortical bone region;
a single continuous thread of uniform pitch extending between the proximal and distal ends; and
a tapered section disposed between the distal threaded section and the distal end that facilitates insertion of the distal end of the interference screw into a bone tunnel, wherein the tapered section is threaded.

19. An interference screw as defined in claim 18, wherein the proximal end is obliquely angled relative to the central axis so that) upon threadably inserting the interference screw into a bone tunnel formed at a predetermined angle relative to a bone surface surrounding the bone tunnel, the proximal end is substantially parallel to the bone surface when the interference screw is oriented at an appropriate rotational angle.

20. An interference screw as defined in claim 18, wherein the proximal threaded section is separated from the distal threaded section by a tapered transition section.

21. An interference screw as defined in claim 18, the single continuous thread having a constant thread depth.

22. An interference screw for cortical and cancellous bone fixation of a soft tissue graft within a bone tunnel, comprising:
a fully threaded body extending between a proximal end and a distal end along a central axis and being sized and configured for threadable insertion into a bone tunnel, the threaded body further comprising:
a proximal threaded section sized and configured so as to lie primarily adjacent to cortical bone when the interference screw is completely inserted into a bone tunnel, the proximal threaded section having an average diameter that is constant throughout at least a portion of the proximal threaded section;
a distal threaded section sized and configured so as to lie primarily adjacent to cancellous bone when the interference screw is completely inserted into a bone tunnel, the distal threaded section having a constant diameter that is less than the diameter of the proximal threaded section,
the interference screw having an overall length in order for the interference screw to apply force along a greater distance in the cancellous bone region compared to the cortical bone region,
the proximal and distal threaded sections being configured in order for the interference screw to apply less pressure against a soft tissue graft within the cancellous bone region compared to the cortical bone region;
a single continuous thread of uniform pitch extending between the proximal and distal ends; and
a recess, extending through the threaded body from the proximal end at least partially toward the distal end, that is sized and configured to receive at least a portion of a drive shaft of a driver.

23. An interference screw as defined in claim 22, the single continuous thread having a constant thread depth.

24. An interference screw as defined in claim 22, the threaded body further comprising a tapered and threaded transition section between the proximal threaded section and the distal threaded section.

25. A method of securing a soft tissue graft against both cortical and cancellous bone tissue within a bone tunnel, comprising:
forming a bone tunnel of constant diameter through a bone so that the bone tunnel is surrounded by a cortical bone region and a cancellous bone region;
inserting a soft tissue graft at least partially through the bone tunnel; and
threadably inserting a single interference screw comprising portions of varying diameter along the length of the interference screw into the bone tunnel the interference screw including a proximal threaded section and a distal threaded section, the proximal thread section having a greater diameter than the distal thread section and distal threaded section having a greater length than proximal threaded section in order for the interference screw to apply a greater compressive force against the soft tissue graft in the cortical bone region of the bone tunnel and a lesser compressive force against the soft tissue graft in the cancellous bone region and in order for the interference screw to apply force along a greater distance in the cancellous bone region compared to the cortical bone region.

26. A method as defined in claim 25, wherein the interference screw comprises at least one of poly-l-lactic acid, titanium, or stainless steel.

27. An interference screw for cortical and cancellous bone fixation of a soft tissue graft within a bone tunnel, comprising:
 a fully threaded body extending between a proximal end and a distal end along a central axis and being sized and configured for threadable insertion into a bone tunnel, the threaded body further comprising:
  a proximal threaded section sized and configured so as to lie primarily adjacent to cortical bone when the interference screw is completely inserted into a bone tunnel, the proximal threaded section comprising a proximal thread having an average diameter;
  a distal threaded section sized and configured so as to lie primarily adjacent to cancellous bone when the interference screw is completely inserted into a bone tunnel, the distal threaded section comprising a distal thread having a constant diameter that is less than the average diameter of the proximal threaded section, the proximal and distal threads having the same pitch,
  the interference screw having an overall length in order for the interference screw to apply force along a greater distance in the cancellous bone region compared to the cortical bone region,
  the proximal and distal threaded sections being configured in order for the interference screw to apply less pressure against a soft tissue graft within the cancellous bone region compared to the cortical bone region;
 a threaded and tapered transition section disposed between the distal and proximal threaded sections and having increasing diameter from the distal threaded section to the proximal threaded section; and
 a tapered end disposed between the distal threaded section and the distal end that facilitates insertion of the distal end of the interference screw into a bone tunnel.

28. An interference screw for cortical and cancellous bone fixation of a soft tissue graft within a bone tunnel, comprising:
 a fully threaded body extending between a proximal end and a distal end along a central axis and being sized and configured for threadable insertion into a bone tunnel, the threaded body further comprising:
  a proximal threaded section sized and configured so as to lie primarily adjacent to cortical bone when the interference screw is completely inserted into a bone tunnel, the proximal threaded section having a constant diameter;
  a distal threaded section sized and configured so as to lie primarily adjacent to cancellous bone when the interference screw is completely inserted into a bone tunnel,
   the distal threaded section having a constant diameter that is less than the constant diameter of the proximal threaded section,
   the interference screw having an overall length in order for the interference screw to apply force along a greater distance in the cancellous bone region compared to the cortical bone regions,
   the proximal and distal threaded sections being configured in order for the interference screw to apply less pressure against a soft tissue graft within the cancellous bone region compared to the cortical bone region;
  a threaded and tapered transition section between the proximal threaded section and the distal threaded section; and
  a single continuous thread of uniform pitch extending between the proximal and distal ends.

29. An interference screw as defined in claim 28, the single continuous thread having a constant thread depth.

30. An interference screw as defined in claim 28, the proximal end having an angle relative to the central axis in a range of about 10° to about 80°.

31. An interference screw as defined in claim 30, wherein the angle of the proximal end corresponds to an angle of a bone tunnel into which the interference screw is threadably inserted so that, upon threadably inserting the interference screw into the bone tunnel, the proximal end lies substantially parallel to a bone surface surrounding the bone tunnel when the interference screw is oriented at art appropriate rotational angle.

32. An interference screw for cortical and cancellous bone fixation of a soft tissue graft within a bone tunnel, comprising:
 a threaded body extending between a proximal end and a distal end along a central axis and being sized and configured for threadable insertion into a bone tunnel, the threaded body further comprising:
  a proximal threaded section sized and configured so as to lie primarily adjacent to cortical bone when the interference screw is completely inserted into a bone tunnel, the proximal threaded section having an average diameter, the proximal threaded section terminating at said proximal end; and
  a distal threaded section sized and configured so as to lie primarily adjacent to cancellous bone when the interference screw is completely inserted into a bone tunnel, the distal threaded section having a constant diameter that is less than the average diameter of the proximal threaded section; and
  a single continuous thread extending between the proximal and distal ends,
  the proximal end terminating said proximal threaded section having an angle relative to the central axis in a range of about 10° to about 80°,
  the proximal and distal threaded sections having the same thread pitch.

* * * * *

UNITED STATES PATENT AND TRADEMARK OFFICE
CERTIFICATE OF CORRECTION

PATENT NO. : 6,953,463 B2
DATED : October 11, 2005
INVENTOR(S) : Hugh S. West, Jr.

It is certified that error appears in the above-identified patent and that said Letters Patent is hereby corrected as shown below:

Column 5,
Line 59, after "within a bone" remove "to".

Column 6,
Lines 34-35, after "distal tip," change "particular" to -- particularly --.
Line 54, after "discontinuous threads" insert -- ) --.

Column 7,
Line 43, after "angle less" insert -- than --.

Column 13,
Line 29, before "diameter" change "avenge" to -- average --.

Column 14,
Line 7, change "that)" to -- that, --.

Column 15,
Line 1, after "bone tunnel" insert -- , --.
Line 3, after "the proximal" change "thread" to -- threaded --.
Line 4, after "the distal" change "thread" to -- threaded --.
Line 5, before "distal threaded" insert -- the --.
Line 6, before "proximal threaded" insert -- the --.
Line 6, after "threaded section" insert -- , --.

Column 16,
Line 35, before "appropriate" change "art" to -- an --.

Signed and Sealed this

Fourteenth Day of March, 2006

JON W. DUDAS
*Director of the United States Patent and Trademark Office*